United States Patent [19]
Glass

[11] Patent Number: 5,279,793
[45] Date of Patent: Jan. 18, 1994

[54] OPTICAL OSMOMETER FOR CHEMICAL DETECTION

[76] Inventor: Alexander J. Glass, 206 Hillcrest Rd., Berkeley, Calif. 94705

[21] Appl. No.: 938,940

[22] Filed: Sep. 1, 1992

[51] Int. Cl.$^5$ .......................................... G01N 21/17
[52] U.S. Cl. ................... 422/82.06; 128/634; 250/227.14; 385/12; 385/13; 422/82.11; 422/82.13
[58] Field of Search ............ 422/82.05–82.08; 250/227.14; 385/12, 13; 128/634

[56] References Cited

U.S. PATENT DOCUMENTS

| Re. 31,879 | 5/1985 | Lübbers et al. | 436/133 |
|---|---|---|---|
| 4,344,438 | 8/1982 | Schultz | 128/634 |
| 4,577,109 | 3/1986 | Hirschfeld | 250/461.1 |
| 4,599,901 | 7/1986 | Hirschfeld | 128/634 X |
| 4,865,995 | 9/1989 | Dairaku | 422/82.05 X |
| 5,015,843 | 5/1991 | Seitz et al. | 422/82.06 X |

FOREIGN PATENT DOCUMENTS 0352610 1/1990 European Pat. Off. .

OTHER PUBLICATIONS

"Optrodes: Chemically Selective Fiber-Optic Sensors", S. M. Angel, Spectroscopy, vol. 2, No. 4, pp. 38–48.
"Sensitivity and Dynamics of Bioreceptor-based Biosensors", Jerome S. Schultz, Annals of the New York Academy of Sciences, vol. 506, pp. 406–414, Nov. 15, 1987.
"An intravascular protein osmometer", John W. Henson and Robert A. Brace, Am. Journal of Physiology, 244, (5), pp. H726–H729.
"Diaphragm size and sensitivity for fiber optic pressure sensors", Gang He and Frank J. Cuomo, SPIE vol. 1584 Fiber Optic and Laser Sensors IX, pp. 152–156 (1991).
"Fiber Optic Accuracy", Promotional Literature of FiberOptic Sensor Technologies, Ann Arbor Mich. describing a fiber optic pressure catheter.
"Optical fiber sensors and systems for industry", Current Advances in Sensors, B. E. Jones Ed., Adam Hilger, Philadelphia, Pa. pp. 63–74.
"Modern Aspects of Membrane Osmometer Design", O. S. Schäffer, Colloid and Polymer Science, 257, pp. 1007–1108.

*Primary Examiner*—Jill A. Johnston
*Attorney, Agent, or Firm*—R. Russel Austin

[57] ABSTRACT

A fiber optic optical osmometer (50) includes a fiber optic probe (20) inserted into a chamber (24) including a filter member (10) and a diaphragm (14) responsive to a pressure change in the chamber. The filter member transmits a fluid including an analyte into the chamber. A reagent within the chamber reacts with the analyte to form a reaction product. The filter member retains the reaction product in the chamber creating a pressure change. The diaphragm is illuminated by light directed to it from the fiber optic probe. Light reflected from the diaphragm is returned via the fiber optic probe to a detector and measurement electronics. As the diaphragm responds to pressure changes in the chamber, light returned to the detector is modulated proportional to the pressure change. The pressure change may be interpreted as a measure of the concentration of the analyte in the fluid.

12 Claims, 3 Drawing Sheets

OPTICAL OSMOMETER FOR CHEMICAL DETECTION

TECHNICAL FIELD OF THE INVENTION

The present invention relates in general to methods of chemical detection. It relates in particular to optical methods of chemical detection.

BACKGROUND ART

Advances in fiber optic technology have stimulated interest in fiber optic chemical sensors (FOCS). In such devices, the presence of a chemical analyte induces a chemical reaction with a reagent. The reaction is detected as a change in an optical signal. In well known fluorescent methods the change in optical signal may be due to fluorescent material resulting from or being stimulated by the chemical reaction.

FOCS, in general, offer the well known advantages of optical fibers, i.e., small size and freedom from electromagnetic interference. For medical applications they offer the advantage of stability and potential for compatibility with a medical environment, either in a laboratory or "in vivo".

Although fluorescence FOCS has been demonstrated for a number of analytes, they exhibit a limited lifetime in certain environments. Dyes, for example, which are often used as sensors are susceptible to photochemical degradation. Additionally, fluorescence sensors require the use of relatively complex signal detection equipment capable of distinguishing a fluorescence signal induced by an analyte from background fluorescence. Concern about background fluorescence limits the use of plastic fibers which may be safer and more economical in many applications such as medical applications. Further, it is difficult to find a reaction for each possible analyte which leads to a fluorescent product, since only about ten percent of all molecules fluoresce.

A paper "An Intravascular Protein Osmometer", J. Hansen and R. Brace, Am. Journal of Physiology, 244 (5) pp H726-729 (1983), describes a device for measuring the concentration of protein in circulating blood, using osmotic pressure. In the Hansen and Brace device, two identical capillary tubes are placed in a sample. One of the tubes is open to sample pressure, while the other is terminated with an osmotic membrane, formed by a dialysis fiber. Osmotic pressure is determined by the difference in pressure in the two capillary tubes. A significant disadvantage of the Hansen and Brace device was that several minutes were required for the pressure to reach equilibrium. The equilibration time could be reduced by increasing the area of the osmotic membrane, but about half of the response time was attributed to the equilibration time within a capillary.

Although osmotic pressure has been used to measure concentrations of analytes of biological and medical interest, well-known methods of measuring osmotic pressure, using a device generally termed an osmometer are, in general, not satisfactory for this purpose, primarily because of shortcomings in common osmometric methods. For example, a review of osmometry by Schaeffer, "Modern Aspects of Membrane Osmometer Design", Colloid and Polymer Science, 257, pp 1007-1108, (1979) identifies the desirability of improvements in osmometric methods such as shorter response time, eliminating a free boundary between a solvent and a solution, a capability to externally modify pressure difference and temperature compensation. Such improvements are indeed required if osmotic pressure measurement is to be commercially useful as a method of chemical detection.

SUMMARY OF THE INVENTION

The present invention is directed to apparatus for detecting the presence and concentration of an analyte in a fluid. The invention comprises a chamber having a reagent therein for reacting with the analyte to form a reaction product. The chamber includes a filter member which will transmit the analyte and the fluid into the chamber to form the reaction product and retain the reaction product in the chamber. Retaining the reaction product creates a pressure change within the chamber proportional to the concentration of the analyte in the fluid.

The chamber includes a pressure sensitive member responsive to a pressure change within the chamber. The apparatus includes optical means for illuminating the pressure sensitive member and receiving an optical signal reflected therefrom. A change in the optical signal is interpreted as a measure of a change in pressure within the chamber.

In a preferred embodiment, the filter member is formed from a semi-permeable dialysis fiber. The fiber forms a wall of the chamber. In one end of the chamber is inserted a fiber optic probe for transmitting and receiving light. At the opposite end of the chamber is a diaphragm which deforms responsive to pressure changes within the chamber. Light is transmitted through the fiber optic probe through the chamber to the diaphragm. Light is reflected from the diaphragm back into the fiber optic probe which transmits it to a detector and associated measurement electronics. As the diaphragm distorts, the amount of light received by the fiber optic changes. The measurement electronics may be calibrated to interpret the change as a direct reading of osmotic pressure or analyte concentration.

In another embodiment of the invention a temperature probe such as a thermocouple may be located in or close to the chamber for determining the temperature within the chamber. The temperature data may be used for temperature correction of measurements made with the apparatus.

Fiber optic probes may include glass or plastic fibers. The apparatus is completely compatible with biological and medical environments may be used for "in vivo" determination of blood chemistry.

The apparatus of the present invention may be used, for example for determining blood glucose. A detection sensitivity of about fifty micromoles per liter (50 $\mu M/l$) is possible.

DESCRIPTION OF THE DRAWINGS

The accompanying drawings, which are incorporated in and constitute a part of the specification, schematically illustrate a preferred embodiment of the present invention, and together with the general description given above and the detailed description of the preferred embodiment given below, serve to explain the principles of the invention.

DESCRIPTION OF PREFERRED EMBODIMENTS

Figure 1:
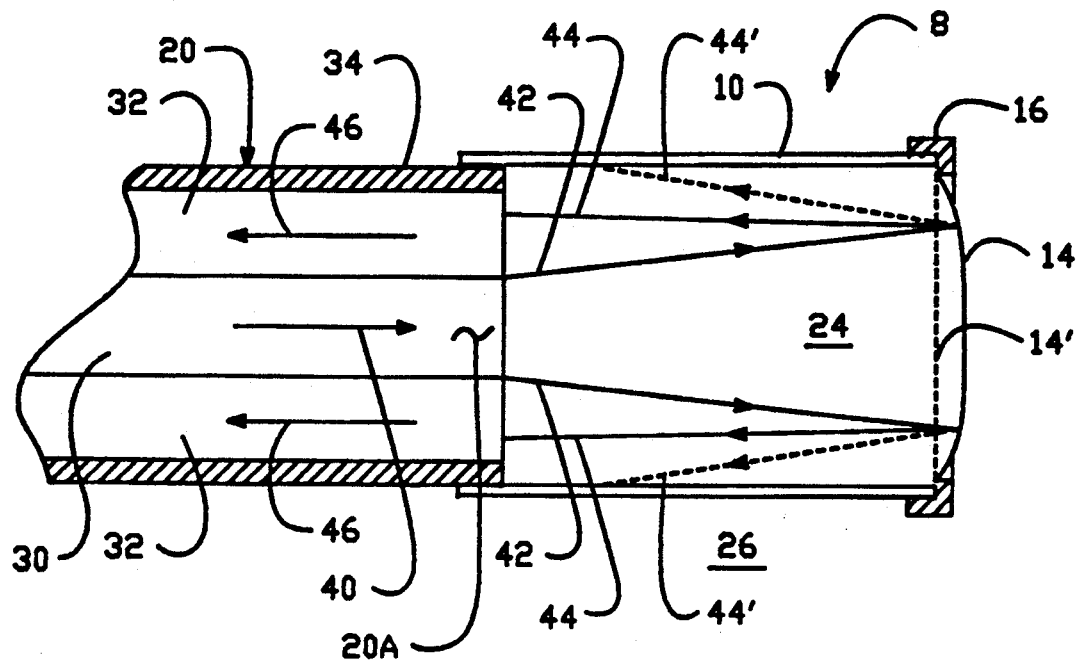
FIG. 1 schematically illustrates one embodiment of a fiber optic probe and osmotic pressure chamber according to the present invention.

Turning now to the drawings wherein like components are designated with like reference numerals, FIG. 1 illustrates one preferred embodiment of a fiber optic osmometer probe 8 according to the present invention. Here a fiber optic bundle 20 is inserted into one end of a segment of a hollow, semi-permeable dialysis fiber 10 such as FIBER CA, available from CD Medical, Inc., of Miami Lakes, FL. A reflective metal diaphragm 14 is clamped by a clamping ring 16 to the other end of the segment of the dialysis fiber. A sensor chamber 24 is formed and enclosed by the end of fiber optic bundle 20, the interior of dialysis fiber 10 and diaphragm 14.

When probe 8 is inserted in a fluid 26 the fluid may enter chamber 24 through dialysis fiber 10. Diaphragm 14 is responsive to pressure changes in chamber 24, i.e. to a pressure difference between fluid in chamber 24 and surrounding fluid 26.

Figure 2:
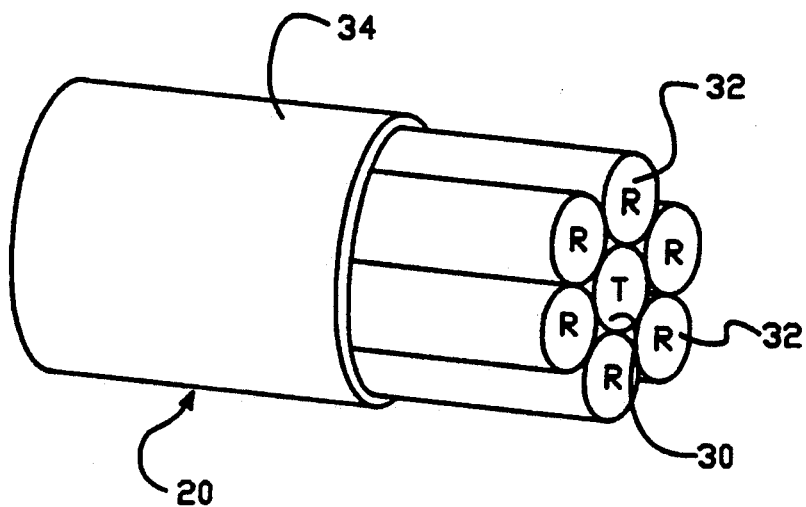
FIG. 2 schematically illustrates details of an arrangement of optical fibers within the fiber optic probe of FIG. 1.

Referring now to FIG. 2 for detail, one embodiment of fiber optic bundle 20 includes a central, light-receiving transmitting fiber 30 surrounded by a plurality of light-receiving fibers 32. Fiber optic bundle 20 may be enclosed by a flexible sheath 34, and at end 20A fibers 30 and 32 are preferably set in a sealing medium such as an epoxy or an elastomer to prevent pressure loss in chamber 24 when the chamber is under pressure.

Referring again to FIG. 1, light 40 from a light source such as a light-emitting diode or a laser may be transmitted down fiber 30. Light 40 emerges from fiber 30 as indicated by rays 42. Rays 42 are incident on reflective diaphragm 14, (shown in FIG. 1 as bowed outward due to positive pressure in chamber 24) and are reflected as rays 44 back into fiber optic bundle 20 via fibers 32. Received light 46 transmitted by fibers 32 provides an optical signal for measuring pressure in chamber 24.

While transmitted light 40 emerges from fiber 30 in a constant pattern, for example, as indicated by rays 42, the pattern of reflected light will vary according to the shape of reflective diaphragm 14, and thus according to the pressure in chamber 24. For example, reflected rays 44' indicate the reflected light pattern from diaphragm 14 when it is flat as indicated in phantom by line 14'. As such, intensity of light received will be modulated by pressure changes within chamber 24 and will thus provide optical means for detecting the pressure changes.

Figure 3:
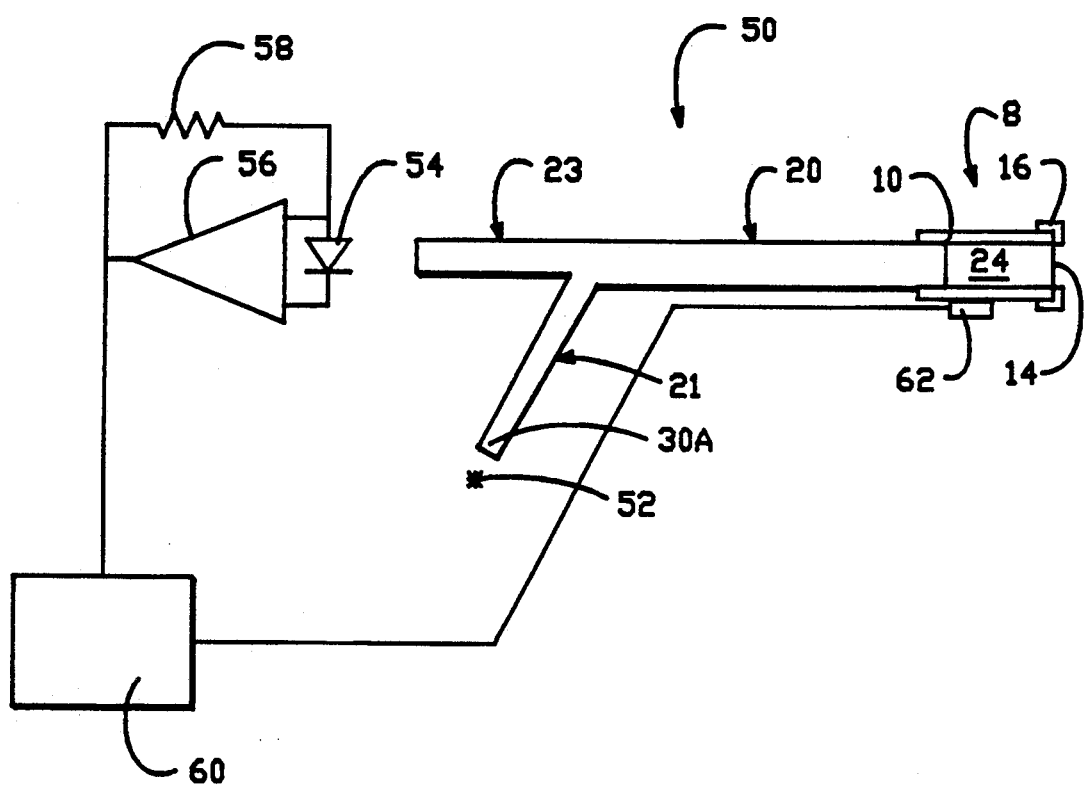
FIG. 3 schematically illustrates a functional diagram of a measurement probe and signal processing electronics.

Turning now to FIG. 3, a fiber optic osmometer system 50 for detecting pressure changes in chamber 24 is shown. System 50 is essentially a fiber optic pressure sensor coupled to osmotic pressure probe 8 including osmotic pressure chamber 24. A fiber optic pressure sensor is commercially available, for example, from Fiber Optic Sensor Technologies, of Ann Arbor, MI. A detailed description of the design and selection of reflective diaphragms for a fiber optic pressure sensor is given in a "Diaphragm size and sensitivity for fiber optic pressure sensors", G. He, et. al., SPIE Vol 1584 Fiber Optic and Laser Sensors IX, pp 152-156 (1991).

In fiber optic osmometer system 50, a light source 52 is directed onto end 30A of fiber 30 (see FIG. 1) which is contained in a branch 21 of fiber bundle 20. Fibers 32 (see FIG. 1) are contained in a branch 23 of fiber bundle 20. Received light 46 from fibers 32 (see FIG. 1) is directed onto an optical detector 54, such as a photo diode. Detector 54 may be provided with a preamplifier 56 and a load resistor 58. Output from preamplifier 56 is directed to signal processing electronics 60 where the output may be calibrated as osmotic pressure or analyte concentration by methods which will be discussed further in subsequent paragraphs. As pressure in chamber 24 is dependent on temperature of fluid surrounding and within chamber 24, a temperature probe 62, such as a fiber optic photoluminescence probe as described by Jones, in "Optical fiber sensors and systems for industry", *Current Advances in Sensors*, B. E. Jones Ed., Adam Hilger, Philadelphia PA (1987), may be placed in the vicinity of chamber 24 to measure the temperature of surrounding fluid. A signal from temperature sensor 62 may be provided to processing electronics 60 for calibrating pressure and concentration measurements.

Referring again to FIG. 1, this description of the of fiber optic osmometer system 50 continues with chemical aspects of the system. In order to provide an osmotic pressure in chamber 24 in the presence of an analyte, a reagent may either immobilized on the interior wall of chamber 24, i.e, on dialysis fiber 10, or contained, in solution, within chamber 24. An analyte contained in surrounding fluid 26 passes freely through the dialysis fiber and reacts with the reagent, releasing an indicator molecule which is then trapped within chamber 24 as it can not pass through dialysis fiber 10. As indicator molecules are trapped within chamber 24, the pressure therein rises and the shape of diaphragm changes in response to the pressure change, i.e. to the pressure difference between fluid in chamber 24 and surrounding fluid 26. This pressure difference is the osmotic pressure in chamber 24.

A reaction which creates such osmotic pressure may be described by reference to a reaction for detecting glucose. Glucose detection is a common use for prior art osmometry, as described in the above-referenced Hansen and Brace paper. A fiber optic glucose sensor based on fluorescence has been described by Schultz in U.S. Pat. No. 4,344,438. Reagents used by Schultz, without attached fluorescent labels, may be used to form a reaction detectable by the optical osmometer of FIG. 1 as described in an example set forth below.

A lectin concanavalin-A (conA) may be immobilized on the inner (chamber side) of dialysis fiber 10. Glucose (the analyte) will pass through dialysis fiber 10 and bind to conA to form an immobilized complex. An indicator, for example, a polysaccharide such as dextran, is contained within the cavity. The dextran will compete with the glucose for binding sites on membrane 10. In the absence of glucose most of the dextran will be bound to the interior of dialysis fiber 10 with only a small residual quantity thereof in the analyte in chamber 24. When glucose is present, the dextran will be displaced into the interior of chamber 24 since it cannot pass through membrane 24. When the dextran is thus trapped in chamber 24 the pressure therein will rise and cause deformation of diaphragm 14 which may be detected optically and interpreted as a change in pressure as described above. The potential sensitivity of the technique may be estimated as set forth below.

For a concentration (c) of solute, in moles/liter (M/1) the osmotic pressure is given by the equation:

$$P = cRT(1 + Bc + Cc^2) \qquad (1)$$

where R is 67.78 liter-torr/mole-degree (the gas constant), and T is the absolute temperature in degrees Kelvin. The coefficients B and C represent a degree of departure of equation (1) from the well-known Van't Hoff Law, to which equation 1 reduces for dilute solutions, i.e. as the concentration c tends to zero. The osmotic pressure of macromolecules of the indicator is affected by their charge and shape such that the value of coefficient B may become significant. Varying the shape and charge of a competing analyte may optimize the value of B and thus the sensitivity of the technique. Based on well-known reactions such as the above described glucose reaction, for example, it is estimated that the present invention may be used to detect solute concentration variations as low as fifty micromoles per liter (50 $\mu$M/1).

The concentration of solute trapped in chamber 24 may be related to the concentration of the analyte in different ways. For example, if a reagent is as described above for the glucose reaction, the concentration of the solute will equal the moles of the indicator displaced into chamber 24 by the analyte, divided by the volume of chamber 24. Here an advantage of the present invention becomes evident as the fiber optic sensor enables a chamber having a very small volume to be provided. For a small chamber, the ratio of the surface area (i.e dialysis fiber area) to chamber volume (A/V) is large, and is given by the equation:

$$(A/V) = 2/r \qquad (2)$$

where r is the radius of cylindrical wall of chamber 24, i.e., the inner radius of dialysis fiber 10 of chamber 24. Thus, if there are $10^{15}$ binding sites per square centimeter on the chamber wall having a radius of about one-hundred micrometers (100 $\mu$m), and ten percent of the sites are taken up by glucose, the resulting solute concentration will be thirty micromoles per liter (30 $\mu$M/1), i.e within the detection sensitivity range for the method of the present invention.

Other reactions which do not involve immobilizing a reagent on a membrane wall are applicable to the present invention. In such a reaction, for example, an indicator may be bound to a reagent which is in solution within chamber 24. Analyte passing through membrane 10 will displace indicator from the reagent into solution the analyte in turn becoming bound to the reagent. In this case the number of free indicator molecules in the solution will be equal to the number of bound analyte molecules. Since the indicator molecules are trapped in chamber 24, an osmotic pressure differential will build up proportional to the concentration of indicator molecules, i.e., proportional to the concentration of analyte molecules. The osmotic pressure build up will cause deflection of diaphragm 14 detectable by optical detector 54.

If a reagent is in solution it is possible to form a multicomplex between the reagent and the indicator. For example, in terms of the above-described glucose reaction, a multicomplex conA-dextran-conA-dextran-conAdextran ... may be formed. In the presence of the analyte, several molecular complexes of the form glucose-conA will, be liberated from a single multicomplex by the competing reaction, thereby enhancing the change in osmotic pressure, and increasing the sensitivity of the sensor.

Figure 4:
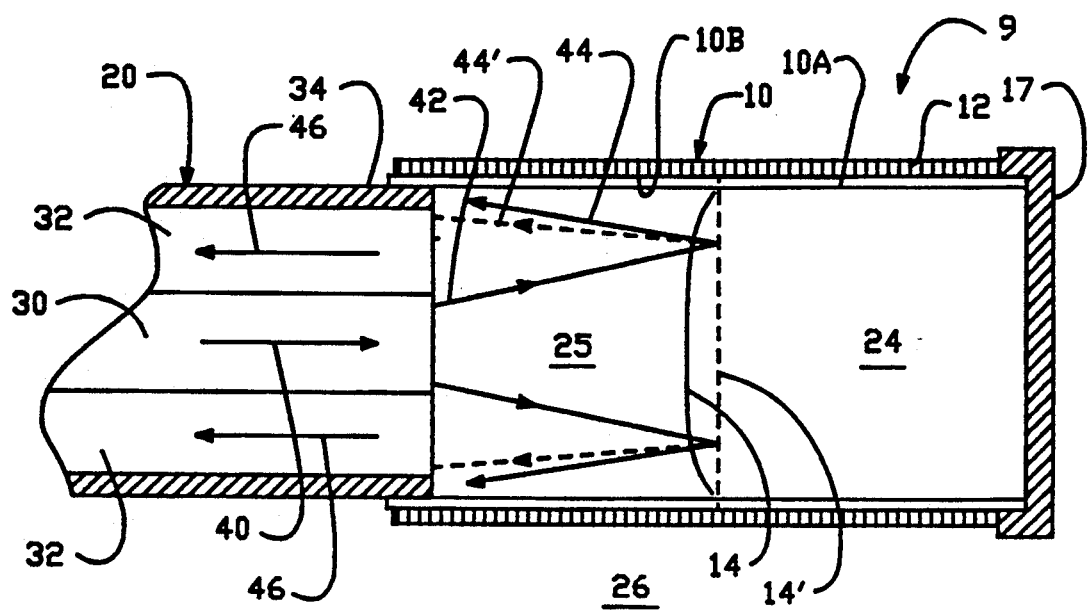
FIG. 4 schematically illustrates another arrangement of a fiber optic probe and osmotic pressure chamber according to the present invention. The arrangement includes means for protecting a pressure sensitive diaphragm.

Turning now to FIG. 4, another embodiment 9 of a fiber optic probe for fiber optic osmometer system 50 is illustrated. Probe 9 is configured for use in cases where an osmotic pressure producing reaction in chamber 24 of probe 8 (FIG. 1) would cause cloudiness of a solution therein. Increasing cloudiness in a solution would cause the solution to increasingly attenuate, i.e., modulate, light passing through the solution. This modulation may be interpreted erroneously as due to a pressure change in the solution. In probe 9, chamber 24, containing a reagent as described above, is joined generally coaxially in an end-to-end relationship with another chamber 25 which does not contain a reagent. Chambers 24 and 25 may be formed by attaching a segment of a semi-permeable dialysis fiber at the end of fiber optic bundle 20. The segment of dialysis fiber is split at about the center and the two halves 10A and 10B of the dialysis fiber separated by a flexible diaphragm 14. The fiber halves and the diaphragm may be secured by a wire mesh cylinder 12 tightly fitting around the outside of the fiber halves. The end of chamber 24 is sealed by an end cap 17.

As chamber 25 does not contain a reagent, fluid 26 may enter and leave 25 at an equal rate through dialysis fiber 10B. As such, the pressure in chamber 25 will be substantially equal to the pressure of surrounding fluid 26. As chamber 24 does contain a reagent a reaction may form in the chamber as fluid 26 enters through dialysis fiber 10A raising the pressure in chamber 24 as described above. Light rays 42 incident on diaphragm 14, and light rays 44 and reflected from diaphragm 14 do not pass through chamber 24, in which a reaction occurs, but through chamber 25 in which the fluid composition is essentially constant. Even if fluid in chamber 25 attenuates light to some degree, this attenuation will remain constant. Thus, any change in the intensity of received light 46 can only result from a change in shape of diaphragm 14 corresponding to a change in pressure in chamber 24.

In above-described embodiments of a fiber optic osmometer system, changes in an optical signal are measured. The changes are representative of a change in osmotic pressure, in turn representative of concentration of an analyte in a fluid. As such, the changes must be calibrated to determine the osmotic pressure and the osmotic pressure in turn must be calibrated or related to analyte concentration.

Figure 5:
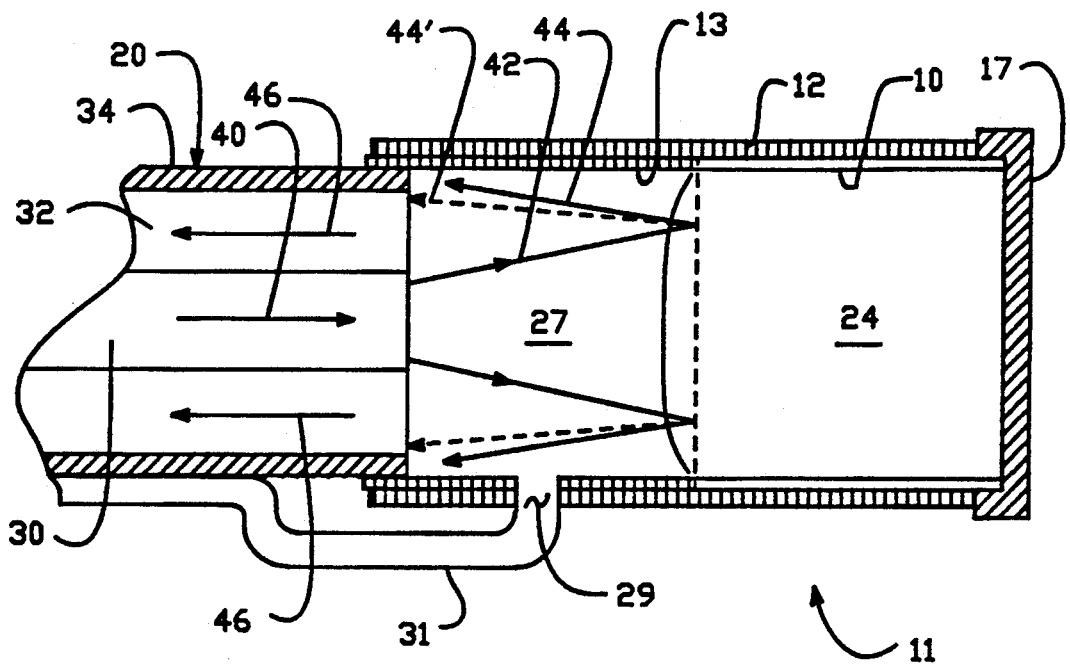
FIG. 5 schematically illustrates yet another arrangement of a fiber optic probe and osmotic pressure chamber according to the present invention. The arrangement includes a pressure source for providing a null measurement.

Turning now to FIG. 5, a fiber optic probe 11 is illustrated which allows osmotic pressure to be measured directly by conventional manometric methods This removes the pressure calibration step required in other embodiments of system 50 and potentially improves accuracy in determining analyte concentration.

In Probe 11, chamber 24, containing a reagent as described above, is attached generally coaxially in an end to end relationship to another chamber 27. Chamber 27 may be formed by an impervious cylinder 13. Chamber 27 has an aperture 29 therein for admitting a fluid. A pressure catheter 31 attached to aperture 29 communicates chamber 27 with a source of fluid (not shown) for filling chamber 27. The fluid source may be pressured and the pressure measured by conventional manometric methods. Chambers 24 and 27 are separated by diaphragm 14 at adjoining ends. At the end of chamber 24 opposite diaphragm 14 is a sealing cap 17. At the end of chamber 27 opposite membrane 14 fiber optic bundle 20 is inserted through an end wall 15.

When probe 11 is inserted in fluid 26 including an analyte, pressure in chamber 24 increases as described above, diaphragm 14 changes shape, and received light 46 changes intensity. The change in intensity may be detected and measured as previously described. Pressure is then applied to the fluid source connected to catheter 31 and is thus communicated to fluid in chamber 27. Pressure in chamber 27 is increased until light 46 is returned to its original intensity. The pressure applied to the fluid source, i.e., to chamber 27 to return light 46 to its original intensity thus provides a direct measure of osmotic pressure, which may be related, as discussed above, to analyte concentration in fluid 26.

Embodiments of a fiber optic optical osmometer system for detecting and measuring concentration of an analyte in a fluid have been described.

A useful feature of the optical osmometer is that many reactions used in FOCS are applicable to the fiber optic osmometer system 50. This allows the system to be evaluated and calibrated against established prior art methods as well as providing an immediate range of analytes that the system is capable of detecting.

The fiber optic optical osmometer system of the present invention is applicable to the measurement of any analyte which reacts with an indicator molecule to form a molecular complex significantly larger than the original analyte molecule. A particularly advantageous feature of the osmometer is the ability to use an enzyme as the indicator, thereby providing an ability to discriminate among chemically similar analytes. Analytes of interest for fermentation, for example are typically organic molecules of similar composition, which are difficult to discriminate among using fluorescence or even Raman techniques. Analytes of interest include glucose, lactate, glutamate, and acetate.

Another useful feature of the optical osmometer is that it is responsive essentially immediately to an osmotic pressure change, and further, the osmotic pressure change may be measured directly. This represents a significant advantage over prior art osmometric methods such as the above-referenced Hansen and Brace method, wherein response time for pressure measurement was on the same order as the response time for osmotic pressure equilibration caused by the osmotic membrane.

Heretofore, because of shortcomings in fluorescence detection methods and in osmometric methods development and optimization of reverse osmosis membranes specifically for chemical detection has been difficult as many of the membrane effects and features have been masked by measurement uncertainties. By significantly reducing measurement response time and measurement uncertainty the present invention provides a means by which reverse osmosis membranes may be optimized and improved for osmometric chemical detection. This provides a potential for making significant progress in the application of osmometry in medical and biological science.

While the present invention has been described in terms of preferred embodiment and other embodiments, various changes and modifications could be made therein by one skilled in the pertinent art without departing from the spirit and scope of the invention as defined by the appended claims.

INDUSTRIAL APPLICATIONS

In a fermentation process, a living organism, which can be a bacterium, a fungus, a yeast, or an isolated mammalian cell, converts a nutrient into a useful product through metabolic action. Examples of fermentation include conversion of sugar, such as glucose, into ethanol or acetic acid. Fermentation processes have long been used in the production of food and beverages. With advances in genetic engineering and cell culture, a new type of fermentation is becoming increasingly commercially, and it is expected that genetically engineered organisms will be widely used in industry for the production of amino acids, pharmaceuticals, and antibodies, in addition to traditional food and beverage products.

Fermentation in mammalian cells require more sophisticated instrumentation than traditional fermentation processes. Mammalian cells are more fragile, and the growth environment needs to be carefully monitored. Further, in many cases, the chemical reactions do not proceed to completion, so that careful and timely monitoring of nutrients, metabolic waste products, and the final product of the fermentation process are required on a continuous basis. The fiber optic osmometer of the present invention is well suited to monitoring the level of products and reagents in a cell culture medium as they are nonelectrical and compact, but still provide data with little delay and good sensitivity.

What is claimed is:

1. An apparatus for detecting concentration of an analyte in a fluid, comprising:
    a chamber having a reagent therein, said chamber including a filter member permeable to the analyte and the fluid;
    said filter member for transmitting the fluid and the analyte into said chamber to react with the reagent and form a concentration of a reaction product proportional to the concentration of the analyte in the fluid;
    said filter member impermeable to said reaction product for retaining said reaction product therein to cause a pressure change in said chamber, said pressure change related to the concentration of reaction product formed;
    said chamber including a pressure sensitive member deformable by said pressure change within said chamber; and
    optical means for illuminating said pressure sensitive member and receiving an optical signal reflected therefrom, said optical means arranged such that deformation of said pressure sensitive member modulates said optical signal, whereby measurement of said optical signal modulation provides a means for determining the concentration of the analyte.

2. The apparatus of claim 1 further including means for computing the analyte concentration from said optical signal modulation.

3. The apparatus of claim 1 further including means for determining the temperature of said chamber.

4. The apparatus of claim 1 wherein said filter member is a dialysis fiber.

5. The apparatus of claim 4 wherein said optical means includes a fiber optic element.

6. The apparatus of claim 5 wherein said pressure sensitive member is a diaphragm.

7. The apparatus of claim 6 further including means for measuring the temperature of said chamber.

8. The apparatus of claim 7 further including means for computing the analyte concentration from said optical signal modulation.

9. An apparatus for detecting concentration of an analyte in a fluid, comprising:

first and second cylindrical chambers joined in an end-to-end relationship and generally coaxial, said chambers separated by a diaphragm deformable by a pressure change in said first chamber;

said first chamber having a reagent therein for reacting with the analyte to form a reaction product, and said first chamber having a generally cylindrical wall including a filter member, said filter member permeable to the analyte and the fluid for transmitting the fluid and the analyte into said chamber to react with the reagent and form a concentration of said reaction product proportional to the concentration of the analyte in the fluid, and said filter member impermeable to said reaction product for retaining said reaction product in said first chamber to cause said pressure change therein, said pressure change related to the concentration of reaction product formed;

said second chamber having a substantially cylindrical wall including a semipermeable filter member; and said second chamber including fiber optic means for illuminating said diaphragm and receiving an optical signal reflected therefrom said fiber optic means arranged such that deformation of said diaphragm modulates said optical signal, whereby measurement of said optical signal modulation provides a means for determining the concentration of the analyte.

10. The apparatus of claim 9 further including means for measuring the temperature of the fluid.

11. The apparatus of claim 9 further including means for detecting said optical signal and means for computing the analyte concentration from said optical signal modulation.

12. An apparatus for detecting the concentration of an analyte in a first fluid, comprising:

first and second cylindrical chamber joined in an end-to-end relationship and generally coaxial, said chambers separated by a diaphragm said diagram having an original shape deformable by a pressure change in said chambers;

said first chamber having a reagent therein for reacting with the analyte to form a reaction product, and said first chamber having a generally cylindrical wall including a semipermeable filter member, said filter member permeable to the analyte and the first fluid for transmitting the first fluid and the analyte into said first chamber to react with the reagent and form a concentration of said reaction product proportional to the concentration of analyte in the fluid, and said filter member impermeable to said reaction product for retaining said reaction product in said first chamber to create a first pressure change therein, said first pressure change related to the concentration of reaction product formed and said first pressure change deforming said diaphragm from said original shape;

said second chamber including fiber optic means for illuminating said diaphragm and receiving an optical signal reflected therefrom, said fiber optic means arranged such that said optical signal changes from a first value to a second value responsive to said deformation of said diaphragm; and said second chamber including means for receiving a measurable fluid pressure to create a measurable second pressure change in said second chamber, said second pressure change equal to said first pressure change for restoring said diaphragm to said original shape, said original shape restoration detectable by a change in said optical signal from said second value to said first value, whereby measurement of said second pressure change provides a means for determining the concentration of the analyte.

* * * * *